United States Patent
Ohta et al.

(10) Patent No.: US 7,125,725 B2
(45) Date of Patent: Oct. 24, 2006

(54) BIARYL-TYPE COMPOUNDS, CD COLOR FIXING AGENT AND METHOD FOR DETERMINATION OF ABSOLUTE CONFIGURATION

(75) Inventors: Tomihisa Ohta, Kanazawa (JP); Shinzo Hosoi, Kanazawa (JP)

(73) Assignee: Kanazawa University, Kanazawa (JP)

( * ) Notice: Subject to any disclaimer, the term of this patent is extended or adjusted under 35 U.S.C. 154(b) by 421 days.

(21) Appl. No.: 10/785,070

(22) Filed: Feb. 25, 2004

(65) Prior Publication Data

US 2004/0171662 A1 Sep. 2, 2004

Related U.S. Application Data

(63) Continuation of application No. 10/082,251, filed on Feb. 26, 2002, now Pat. No. 6,727,098.

(30) Foreign Application Priority Data

Jun. 21, 2001 (JP) .............................. 2001-187770

(51) Int. Cl.
*G01N 33/00* (2006.01)
(52) U.S. Cl. ........................ 436/111; 436/120; 436/131; 436/171; 548/266.8; 548/269.4; 548/341.5; 548/346.1; 548/354.1

(58) Field of Classification Search ................ 436/111, 436/120, 131, 171; 548/266.8, 269.4, 341.5, 548/346.1, 354.1
See application file for complete search history.

(56) References Cited

FOREIGN PATENT DOCUMENTS

| JP | 63-132795 A2 | 6/1988 |
|----|--------------|--------|
| JP | 2001-220392  | 8/2001 |

OTHER PUBLICATIONS

Hosoi, "NOvel Development of Exciton-Coupled Circular Dichroism Based on Induced Axial Chirality", Organic Letters, vol. 3, No. 23, pp. 3659-3662, 2001.*

Hosoi et al., "Chirality transmission in flexible 5,5'-dinitrodiphenic esters connected with chiral secondary alcohols", Tetrahedron Letters 42 (2001) 6315-6317.

Hosoi et al., "Novel Development of Exciton-Coupled Circular Dichroism Based on Induced Axial Chirality", Organic Letters, vol. 3, No. 23, pp. 3659-3662, 2001.

* cited by examiner

*Primary Examiner*—D. Margaret Seaman
(74) *Attorney, Agent, or Firm*—Oliff & Berridge, PLC

(57) ABSTRACT

A novel achiral biaryl-type compound and a circular dichroism(CD) color fixing agent are provided. Furthermore, a method for determining an absolute configuration of a chiral compound is carried out by introducing the above achiral biaryl-type compound into the chiral compound.

3 Claims, 6 Drawing Sheets

BIARYL-TYPE COMPOUNDS, CD COLOR FIXING AGENT AND METHOD FOR DETERMINATION OF ABSOLUTE CONFIGURATION

This is a Continuation of application Ser. No. 10/082,251 filed Feb. 26, 2002 now U.S. Pat. No. 6,727,098. The entire disclosure of the prior application is hereby incorporated by reference herein in its entirety.

BACKGROUND OF THE INVENTION

1. Field of the Invention

This invention relates to a biaryl-type compound, a circular dichroism (CD) color fixing-agent for introducing a CD chromophore into a chiral compound and a method for determination of absolute configuration of a chiral compound.

2. Description of Related Art

In compounds having a single functional group such as alcohols, thiols, amines and the like is included a compound having an optical activity referred to as a chiral compound. There are known various methods in order to determine an absolute configuration of such a chiral compound.

Among them, a modified Mosher method using NMR is used most practically and frequently at the present time.

And also, a method using CD is known in the determination of the absolute configuration. As to such a method for the determination of the absolute configuration, there are several reports. For example, Harada et al. of Tohoku University of Japan reports that by condensing a chiral alcohol with di(1-naphthyl) acetic acid as a CD auxiliary group is observed a good correlation between the absolute configuration and sign of exciton chirality (40th natural organic compounds symposia).

Furthermore, Adam W. et al. reports that in case of a chiral benzyl alcohol, by newly introducing a benzoyl group is observed a good correlation between sign of Cotton effect indicated by the obtained benzoate body and the absolute configuration [Journal of Organic Chemistry, 65, pp 186–190 (2000)].

However, the modified Mosher method becomes complicated in the operation of determining the absolute configuration and requires at least a few milligram of a sample.

The method of Harada et al. is insufficient in the yield of the derivative and further requires the calculation of a stable conformation through a molecular force-field calculation, so that it has a problem that multistage operations are required in the determination of the absolute configuration.

Furthermore, the method of Adam et al. requires the calculation of the stable conformation likewise the above method, and has a problem that an application range of the chiral compound is restricted.

Since the CD exciton chirality method is based on the interaction of two chromophoric excitons, an application to a compound having two or more functional groups such as diol or the like is restricted.

SUMMARY OF THE INVENTION

An object of the invention is to provide a new biaryl-type compound.

Another object of the invention is to provide a new CD color fixing agent by introducing a CD chromophore into a chiral compound.

The other object of the invention is to provide a method for efficiently determining an absolute configuration of a chiral compound.

According to a first aspect of the invention, there is the provision of an achiral biaryl-type compound in which the biaryl-type compound is at least one compound selected from the group consisting of a biphenyl dicarboxylic acid derivative represented by the following general formula (I):

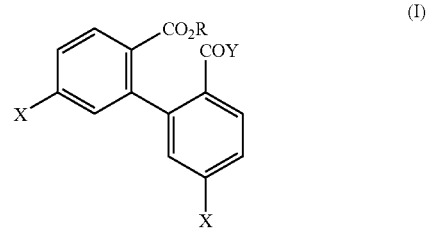

(wherein R is H, Me-, Et-, i-Pr—, n-Bu-, i-Bu- or t-Bu- and X is H, Me-, $Me_2N$—, MeO—, $NO_2$—, $NH_2$—, CN—, Cl or Br, and Y is OH—, CN—,

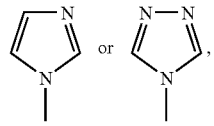

provided that X is $Me_2N$— or CN— when R=H and Y=OH, X is Me-, $Me_2N$—, $NO_2$—, $NH_2$— or CN— when R=Me and Y=OH, and X is Me-, $Me_2N$—, MeO—, $NO_2$—, $NH_2$— or CN— when R=Et and Y=OH, and R is t-Bu- when X=H and Y=OH), 2,2'-binaphthyl dicarboxylic acid derivative represented by the following general formula (II):

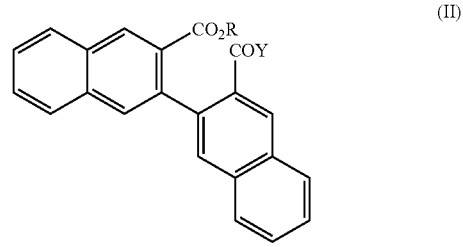

(wherein R is H, Me-, Et-, i-Pr—, n-Bu-, i-Bu- or t-Bu- and Y is OH—, CN—,

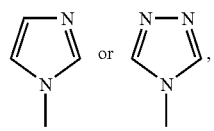

provided that R is i-Pr—, n-Bu-, i-Bu- or t-Bu- when Y=OH), 2,2'-biquinoline dicarboxylic acid and derivatives thereof represented by the following general formula (III):

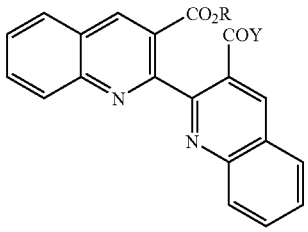

(III)

(wherein R is H, Me-, Et-, i-Pr—, n-Bu-, i-Bu- or t-Bu- and Y is OH—, CN—,

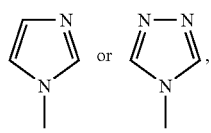

and may contain a compound formed by cyclizing —CO₂R with —COY to form

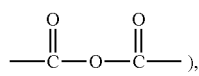), 7,7'-biquinoline dicarboxylic acid and derivatives thereof represented by the following general formula (IV):

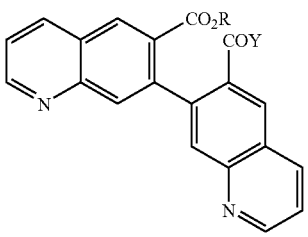

(IV)

(wherein R is H, Me-, Et-, i-Pr—, n-Bu-, i-Bu- or t-Bu- and Y is OH—, CN—,

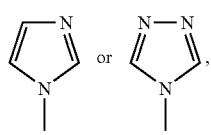

and may contain a compound formed by cyclizing —CO₂R with —COY to form

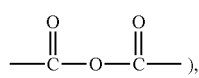), 2,2'-bianthracene dicarboxylic acid and derivatives thereof represented by the following general formula (V):

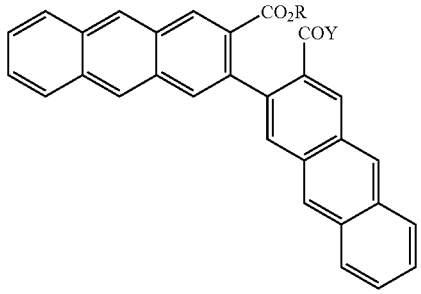

(V)

(wherein R is H, Me-, Et-, i-Pr—, n-Bu-, i-Bu- or t-Bu- and Y is OH—, CN—,

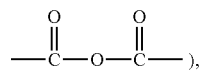

and may contain a compound formed by cyclizing —CO₂R with —COY to form

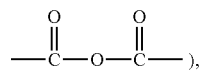), 2,2'-bibenzo(g)quinoline dicarboxylic acid and derivatives thereof represented by the following general formula (VI):

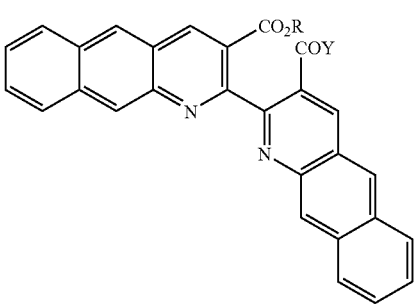

(VI)

(wherein R is H, Me-, Et-, i-Pr—, n-Bu-, i-Bu- or t-Bu- and Y is OH—, CN—,

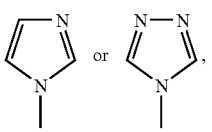

and may contain a compound formed by cyclizing —CO₂R with —COY to form

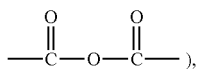

and 3,3'-biacridine dicarboxylic acid and derivatives thereof represented by the following general formula (VII):

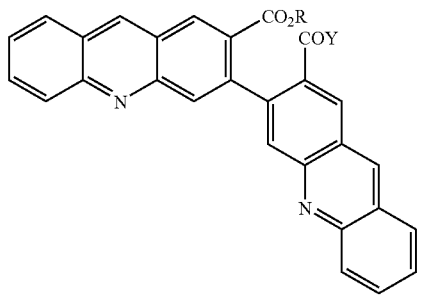

(VII)

(wherein R is H, Me-, Et-, i-Pr—, n-Bu-, i-Bu- or t-Bu- and Y is OH, CN,

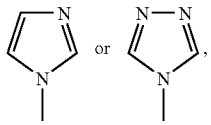

and may contain a compound formed by cyclizing —CO$_2$R with —COY to form

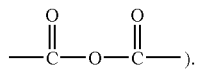

According to a second aspect of the invention, there is the provision of a circular dichroism (CD) color fixing agent for introducing an achiral CD chromophore into a chiral compound, in which the chiral compound is selected from the group consisting of alcohols, thiols and amines, and the CD color fixing agent comprises at least one achiral biaryl-type compound selected from the group consisting of 2,2'-binaphthyl dicarboxylic acid, 2,2'-biquinoline dicarboxylic acid, 7,7'-biquinoline dicarboxylic acid, 2,2'-bianthracene dicarboxylic acid, 2,2'-bibenzo(g)quinoline dicarboxylic acid, 3,3'-biacridine dicarboxylic acid and derivatives thereof and a biphenyl dicarboxylic acid derivative other than biphenyl dicarboxylic acid anhydride.

According to a third aspect of the invention, there is the provision of a method for determining an absolute configuration of a chiral compound, which comprises steps of:
(a) selecting a chiral compound from the group consisting of alcohols, thiols and amines;
(b) introducing an achiral CD chromophore into the chiral compound; and
(c) determining an absolute configuration of the chiral compound from relative bulkiness of a substituent on α-carbon, preferential order in a sequence rule (CIP method) and sign of exciton chirality.

The inventors have reexamined the conventional methods of forming derivatives of chiral compounds and made various improvements thereof in order to efficiently conduct a determination of an absolute configuration of the chiral compound.

As a result, the inventors have found out that a derivative of a chiral compound can be simply formed in a higher yield by introducing an achiral biaryl-type chromophore into a given chiral compound.

Moreover, the inventors have discovered that the absolute configuration of the chiral compound can be determined very simply and efficiently based on a correlation between CD spectrum of such a derivative of the chiral compound and absolute configuration of the chiral compound, and as a result, the invention has been accomplished.

Recently, the inventors developed a CD derivative-forming reagent (biphenyldicarboxylic acid anhydride) applicable to a mono-alcohol, and reported its usefulness in the determination of an absolute configuration (the collection of the 42nd natural organic compound debate lecture summaries, page 571, October, 2000, Okinawa, Japan).

Now, the inventors develop a new reagent capable of more simply forming a derivative from a given chiral compound in a higher yield, and first elucidate a correlation among an absolute configuration of a chiral compound, a relative bulkiness of a substituent on α-carbon, preferential order in a sequence rule, and CD spectrum of a derivative.

The given achiral biaryl-type compounds are novel substances and first discovered in the invention.

And also, the given achiral biaryl-type compound according to the invention can constitute a CD color fixing reagent very useful for the derivative formation of the chiral compound and the determination of absolute configuration thereof.

In the method for the determination of absolute configuration according to the invention, an achiral chromophore is introduced into the given chiral compound. Such an achiral chromophore induces CD in the chiral compound.

In the invention, the achiral chromophore is a material in which a chirality of the chiral compound can be effectively propagated to efficiently determine the absolute configuration of the chiral compound.

The achiral biaryl-type compound, especially CD color fixing agent according to the invention is made possible to simply form a derivative of the chiral compound as a substrate in a high yield to conduct a very efficient determination of absolute configuration.

Moreover, the method for the determination of absolute configuration according to the invention can directly determine the absolute configuration of the chiral compound from a correlation among relative bulkiness of a substituent on α-carbon, preferential order in a sequence rule and sign of exciton chirality without requiring molecular force-field calculation as in the conventional method.

BRIEF DESCRIPTION OF THE DRAWINGS

The invention will be described with reference to the accompanying drawings, wherein.

Figure 1:
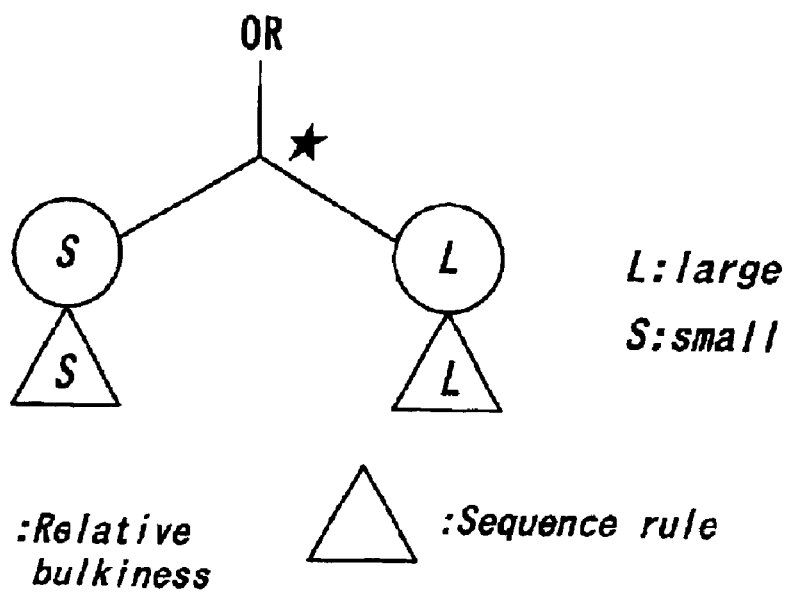
FIG. 1 is a schematic view-showing a relation between relative bulkiness and sequence rule in an embodiment.

DETAILED DESCRIPTION OF THE INVENTION (1) Achiral Biaryl-Type Compound

In the invention, the achiral biaryl-type compounds represented by the formulae (I)–(VII) are novel compounds.

And also, the given achiral biaryl-type compounds according to the invention can introduce a CD chromophore into a chiral compound, and can constitute a CD color fixing agent useful for the derivative formation and the absolute configuration determination of the chiral compound.

The achiral biaryl-type compound constituting such a CD color fixing agent is at least one compound selected from the group consisting of 2,2'-binaphthyl dicarboxylic acid, 2,2'-biquinoline dicarboxylic acid, 7,7'-biquinoline dicarboxylic acid, 2,2'-bianthracene dicarboxylic acid, 2,2'-bibenzo(g)quinoline dicarboxylic acid, 3,3'-biacridine dicarboxylic acid and derivatives thereof and biphenyl dicarboxylic acid derivatives (other than biphenyl dicarboxylic anhydride).

The achiral biaryl-type compound according to the invention can be manufactured according to starting materials and methods described in the known references. As such references, there are, for example, E. J. Moriconi and L. Salce, J. Org. Chem., 32, pp. 2829–2837 (1967), R. G. R. Bacon and R. Bankhead, J. Chem. Soc., pp. 839–845 (1963), C. S. Marvel and L. A. Patterson, J. Am. Chem. Soc., 63, pp. 2218–2220 (1941) and J. Goto, N. Goto, F. Shamsa, M. Saito, S. Komatsu, K. Suzuki, T. Nambara, Anal. Chim. Acta, 147, pp. 397–400 (1983), etc.

(2) CD Color Fixing Agent

The CD color fixing agent according to the invention acts to introduce a CD chromophore into the chiral compound. Such a CD color fixing agent can be offered as a reagent containing the given achiral biaryl-type compound.

According to the kind of achiral biaryl-type compound, the CD color fixing agent can be classified into at least one of biphenyl-type color fixing agent, binaphthyl-type-color fixing agent, biquinoline-type color fixing agent, bianthracene-type color fixing agent, bibenzoquinoline-type color fixing agent, and biacridine-type color fixing agent and so on.

(2-1) Chiral Compound

The chiral compound according the invention is a compound itself giving no clear CD curve. Such chiral compounds are at least one compound selected from the group consisting of alcohols, thiols and amines.

The chiral compound is required to determine the absolute configuration after a clear CD curve is obtained by introducing a suitable CD chromophore into the chiral compound to form a derivative thereof. The chiral compound is not particularly limited in the kind, molecular weight and the like. And also, the chiral compound may be natural or artificial.

(2-2) Derivative Formation of Chiral Compound

In the invention, the derivative of the chiral compound can be formed simply in a higher yield by introducing a CD chromophore into the chiral compound.

The formation of such a derivative is conducted by reacting a chiral compound with a CD color fixing agent. The forming conditions of the derivative can be variously set in base, temperature, time and the like according to a reaction style between the chiral compound and the CD color fixing agent.

In the invention, when each of various alcohols, thiols or amines is reacted with a binaphtyl-type color fixing agent, the corresponding derivative can be obtained at one stage in a high yield by agitating at a room temperature in acetonitril.

(2-3) CD Chromophore

In the invention, CD chromophore to be introduced into the chiral compound is determined according to the kind of the achiral biaryl-type compound used for CD color fixing agent.

The CD chromophore according to the invention can be classified into at least one of biphenyl-type chromophore, binaphthyl-type chromophore, biquinoline-type chromophore, bianthracene-type chromophore, bibenzoquinoline-type chromophore, and biacridine-type chromophore and so on in accordance with the kind of biaryl-type compound.

(2-4) Derivative Formation of Chiral Secondary Alcohol

In the invention, a chiral secondary alcohol can be formed into a derivative with a given CD color fixing agent.

For example, a derivative of a chiral secondary alcohol can be formed as shown by the following reaction formula:

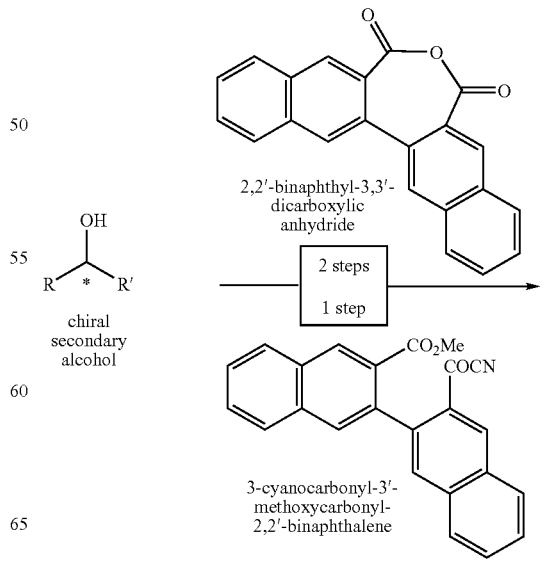

One example of method for determiation of absolute configration according to the present invention -continued

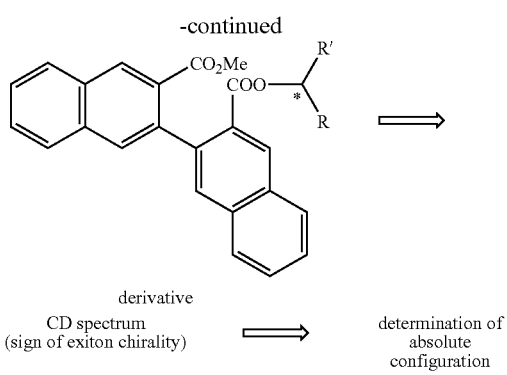

derivative
CD spectrum
(sign of exiton chirality) ⟹ determination of absolute configuration (wherein R and R' are various groups such as an alkyl group, an alkylene group, an aryl group and the like, respectively).

Moreover, the derivative formation of the chiral secondary alcohol through 2,2'-binaphthyl-3,3'-dicarboxylic anhydride in the above reaction formula is preferable to be conducted at two stage of chromophore introduction and methylation because a remarkably clear CD is induced by the methylation.

On the other hand, the derivative formation of the chiral secondary alcohol through 3-cyanocarbonyl-3'-methoxycarbonyl-2,2'-binaphthalene is possible at one stage of chromophore introduction.

In the invention, the absolute configuration of the chiral compound can be determined very efficiently by measuring a CD spectrum of a derivative (sign of exciton chirality) as shown in the above reaction formula and mentioned later in detail.

(3) Method for Determination of Absolute Configuration

In the invention, the absolute configuration of the chiral compound can be efficiently determined based on a correlation between CD spectrum and absolute configuration of the derivative of the chiral compound. Such a method of determining the absolute configuration is based on the exciton chirality method, so that the molecular force-field calculation as in the conventional method is not required and an operation of determining the absolute configuration is very simple.

(3-1) Induced CD

The achiral CD chromophore according to the invention induces a clear CD capable of determining the absolute configuration of the chiral compound in the derivative of the chiral compound.

In the invention, if it is possible to effectively propagate the chirality of the chiral compound to efficiently determine the absolute configuration of the chiral compound, the kind and the like of the achiral CD chromophores are not restricted especially.

For example, a biaryl-type chromophore can be used. The biaryl-type chromophore can be introduced into the chiral compound by reacting the biaryl-type compound with the chiral compound. As the biaryl-type compound may be used a compound as mentioned above.

In the invention, a chirality of a:chiral compound is effectively propagated to the CD chromophore of the derivative of the chiral compound. That is, according to the invention, the exciton chirality of the derivative reflects the chirality of the chiral compound.

(3-2) Relation Between Exciton Chirality of Derivative and Absolute Configuration of Chiral Compound In the invention, the chiral compound is rendered into a derivative with a given chromophore. According to the invention, the exciton chirality of this derivative is decided by the kind of chromophore and the chirality of the chiral compound.

That is, according to the invention, the absolute configuration of the chiral compound can be determined based on the kind of the introduced chromophore by measuring the exciton chirality of the derivative.

For example, in a given chiral compound, a certain chromophore makes the exciton chirality of the derivative to plus (+). And also, in another given chiral compound, another chromophore makes the exciton chirality of the derivative to minus (−).

(3-3) Relative Bulkiness of Substituent on α-Carbon

In the invention, the absolute configuration of the chiral compound to be targeted can be determined based on a relation among relative bulkiness of a substituent on α-carbon, preferential order in a sequence rule and sign of exciton chirality.

In the invention, a bulkiness of a substituent means a van der Waals volume of the substituent on α-carbon. For example, when a molecule to be targeted is a chiral alcohol, a van der Waals volume of a substituent cut at a plane defined by carbinyl C—H bond and C—O bond is a bulkiness of the substituent.

Moreover, a relative bulkiness of a substituent in the invention is shown by relatively large and small when comparing bulkinesses of substituents on α-carbon. That is., as the number of atoms constituting the substituent becomes large, the substituent is more bulky and is considered as large. For example, when a molecule to be targeted is a chiral alcohol, the large or small is shown by comparing bulkinesses of two substituents located at both sides of carbinol carbon.

For example, in case of a compound 1 represented by the following formula (VIII):

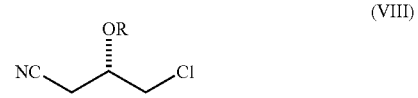

(VIII)

(wherein R is a group represented by the following formula (IX):

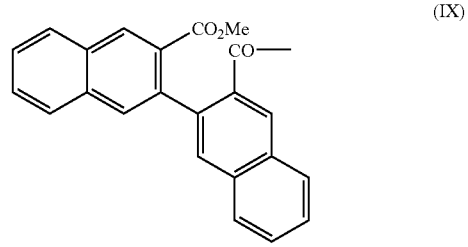

(IX)

it is considered that CN group becomes more bulky because CN group is a substituent consisting of two atoms and Cl group is a substituent consisting of one atom.

(3-4) Preferential Order in Sequence Rule

In the invention, a sequence rule means a code of nomenclature defining a procedure for ranking coordination groups around a chirality element to each other to define an absolute configuration of a chiral molecule.

Moreover, according to the invention, a substituent is shown by large or small based on a preferential order in the sequence rule. A substituent of a high preferential order is called to be large and a substituent of a low preferential order is called to be small.

Figure 2:
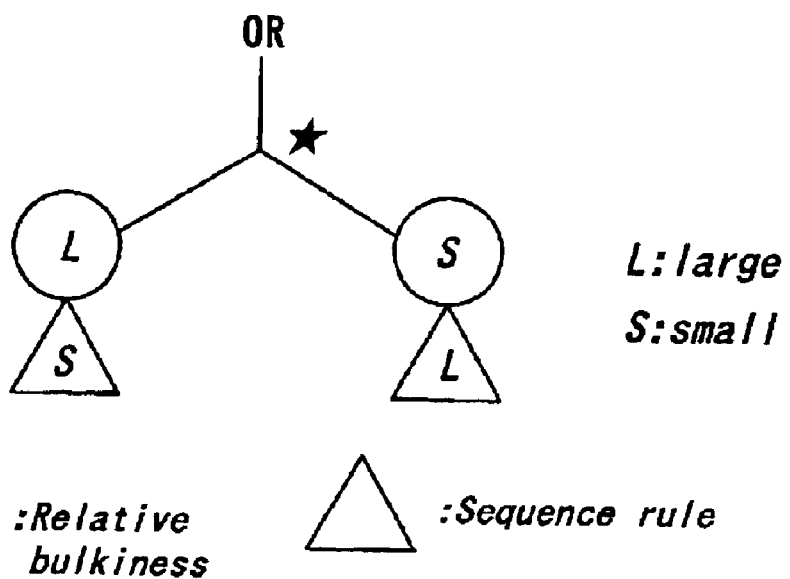
FIG. 2 is a schematic view showing a relation between relative bulkiness and sequence rule in another embodiment.

A relation between relative bulkiness and sequence rule is shown in FIGS. 1 and 2. FIG. 1 is a schematic view showing a relation between relative bulkiness and sequence rule in an embodiment. FIG. 2 is a schematic view showing a relation between relative bulkiness and sequence rule in another embodiment.

In FIG. 1, the large and small relation based on a relative bulkiness of a substituent is the same as the large and small relation based on a sequence rule. In FIG. 2, the large and small relation based on a relative bulkiness of a substituent is opposite to the large and small relation based on a sequence rule.

(3-5) Sign of Exciton Chirality

Under the relation of FIG. 1, a relation between exciton chirality and absolute configuration comes to indicate in Table 1.

TABLE 1

|  | Case 1 | Case 2 |
|---|---|---|
| Sign of exciton chirality | + | − |
| Absolute configuration | S | R |

That is, when the large and small relations of bulkiness and sequence rule are the same, if a sign of exciton chirality is plus, an absolute configuration of an alcohol to be targeted is an S configuration (case 1), while if a sign of exciton chirality is minus, it is an R configuration (case 2).

On the other hand, under the relation of FIG. 2, the relation between exciton chirality and absolute configuration comes to indicate in Table 2.

TABLE 2

|  | Case 3 | Case 4 |
|---|---|---|
| Sign of exciton chirality | + | − |
| Absolute configuration | R | S |

That is, when the large and small relations of bulkiness and sequence rule are opposite, if a sign of exciton chirality is plus, an absolute configuration of an alcohol to be targeted is an R configuration (case 3), while if a sign of exciton chirality is minus, it is an S configuration (case 4).

The method of determining the absolute configuration according to the invention is described by taking a concrete application example.

APPLICATION EXAMPLE 1

In a compound 2 represented by the following formula (X):

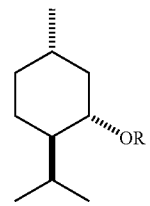

(wherein R is the same as in the formula (IX)), the large and small relation between bulkiness of a substituent and preferential order in a sequence rule is the same. And also, the compound 2 corresponds to the case 1 because a sign of exciton chirality is plus. Therefore, an absolute configuration to be measured is an S configuration.

APPLICATION EXAMPLE 2

In a compound 3 represented by the following formula (XI):

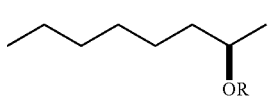

(wherein R is the same as in the formula (IX)), the large and small relation between bulkiness of a substituent and preferential order in a sequence rule is the same. Moreover, the compound 3 corresponds to the case 2 because a sign of exciton chirality is minus. Therefore, an absolute configuration to be measured is an R configuration.

APPLICATION EXAMPLE 3

In a compound 4 represented by the following formula (XII):

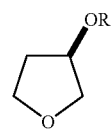

(wherein R is the same as in the formula (IX)), the large and small relation between bulkiness of a subsituent and preferential order in a sequence rule is opposite. And also, the compound 4 corresponds to the case 3 because a sign of exciton chirality is plus. Therefore, an absolute configuration to be measured is an R configuration.

APPLICATION EXAMPLE 4

In the aforementioned compound 1, the large and small relation between bulkiness of a substituent and preferential order in a sequence rule is opposite. And also, the compound 1 corresponds to the case 4 because a sign of exciton chirality is minus. Therefore, an absolute configuration to be measured is an S configuration.

When a chiral compound to be targeted is an alcohol, the large and small relation between bulkiness of a substituent and preferential order in a sequence rule according to the invention can be determined according to a structure in a site adjacent to a carbinol carbon atom.

That is, the absolute configuration can be determined according to the structure in the site adjacent to the carbinol carbon atom in the invention.

Compounds having no electronegative atom such as an unsaturated functional group or an oxygen atom in the site adjacent to the carbinol carbon atom (the large and small relation between bulkiness of a substituent and preferential order in a sequence rule is the same) are a group A, while compounds having an electronegative atom such as an unsaturated functional group or an oxygen atom in the site adjacent to the carbinol carbon atom (the large and small relation between bulkiness of a substituent and preferential order in a sequence rule is opposite) are a group B.

In the group A, a sign of exciton chirality of a chiral compound such as (S)-alcohol or the like is plus, while a sign of exciton chirality of a chiral compound such as (R)-alcohol or the like is minus. On the other hand, the relation of the sign in the group B is opposite to the case of the group A.

Thus, in the invention, the absolute configuration of the chiral compound can be determined based on the correlation between the aforementioned absolute configuration and the sign of exciton chirality.

The method for the determination of absolute configuration according to the invention is very useful in a field mainly developing foods, medicines and so on or a filed manufacturing or analyzing optically active substances.

For example, in the method for the determination of absolute configuration according to the invention, absolute configurations of various chiral alcohols such as 17,18-dihydroxybergamottin and so on providing no clear CD curve can be efficiently determined from a structure in a site adjacent to a carbinol carbon atom and a sign of exciton chirality of a derivative.

The invention is described with respect to examples with reference to the drawings.

Figure 3:
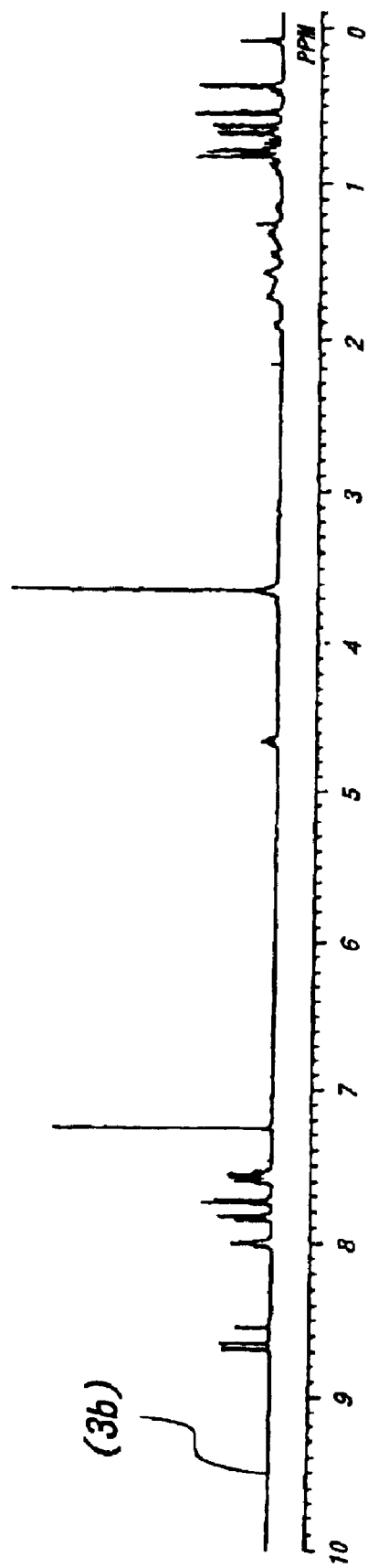
FIG. 3 is a $^1$H-NMR spectrum of an ester (3b)
Figure 4:
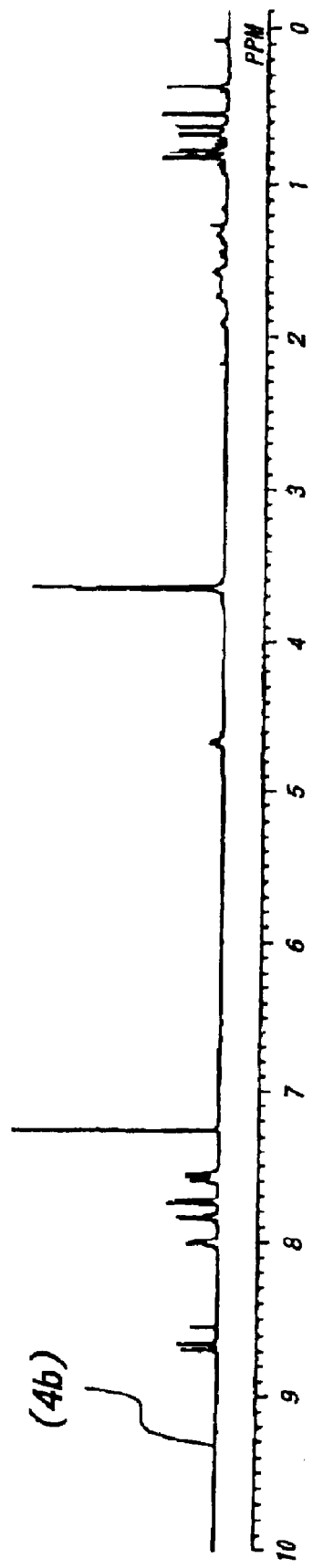
FIG. 4 is a $^1$H-NMR spectrum of an ester (4b)
Figure 5:
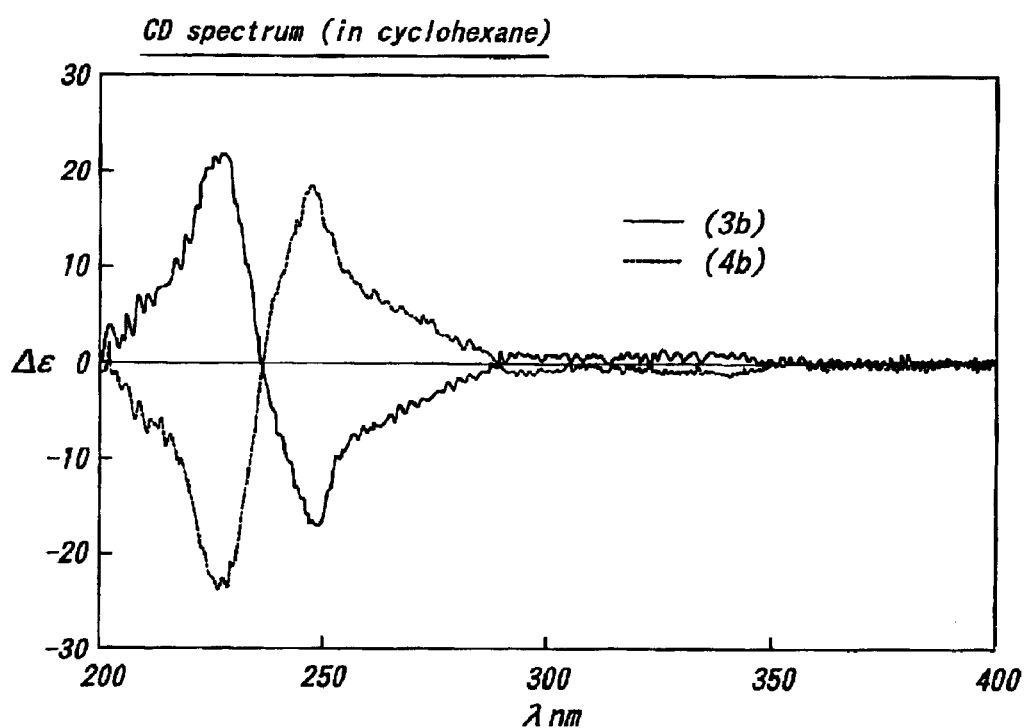
FIG. 5 is CD spectra of esters (3b) and (4b)

FIG. 3 is a $^1$H-NMR spectrum of an ester (3b). FIG. 4 is a $^1$H-NMR spectrum of an ester (4b). FIG. 5 is CD spectra of the esters (3b) and (4b).

Figure 6A:
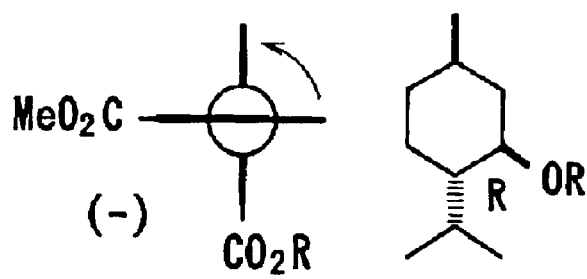
FIG. 6a is a schematic view showing a most stable conformation of an ester (3)
Figure 6B:
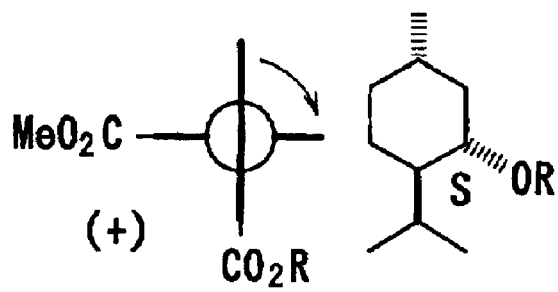
FIG. 6b is a schematic view showing a most stable conformation of an ester (4b)
Figure 6C:
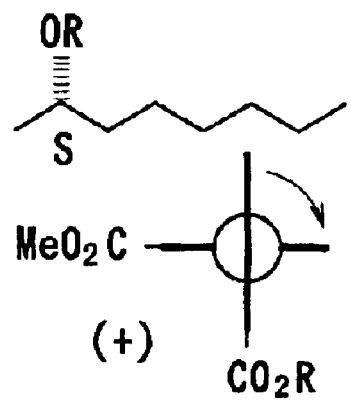
FIG. 6c is a schematic view showing a most stable conformation of an ester (5b)
Figure 6D:
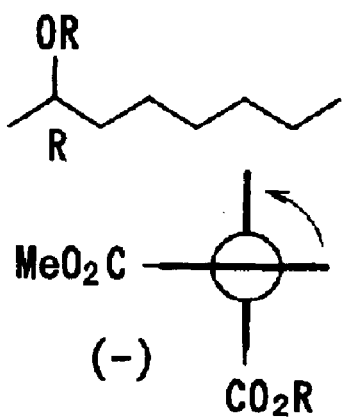
FIG. 6d is a schematic view showing a most stable conformation of an ester (6b)

FIG. 6a is a schematic view showing a most stable conformation of the ester (3b), FIG. 6b is a schematic view showing a most stable conformation of the ester (4b), FIG. 6c is a schematic view showing a most stable conformation of an ester (5b), and FIG. 6d is a schematic view showing a most stable conformation of an ester (6b).

Figure 7A:
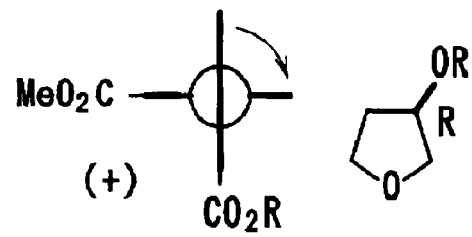
FIG. 7a is a schematic view showing a most stable conformation of an ester (2b)
Figure 7B:
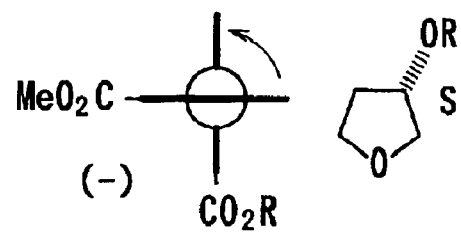
FIG. 7b is a schematic view showing a most stable conformation of an ester (11b)
Figure 7C:
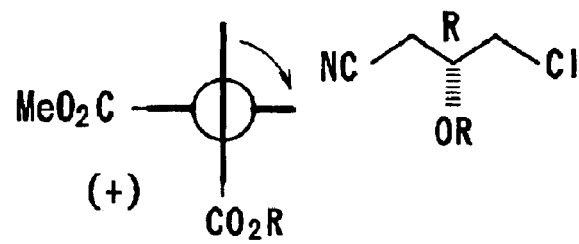
FIG. 7c is a schematic view showing a most stable conformation of an ester (12b)
Figure 7D:
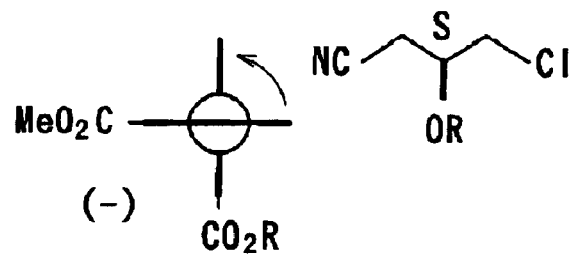
FIG. 7d is a schematic view showing a most stable conformation of an ester (13b).

FIG. 7a is a schematic view showing a most stable conformation of an ester (2b), FIG. 7b is a schematic view showing a most stable conformation of an ester (11b), FIG. 7c is a schematic view showing a most stable conformation of an ester (12b), and FIG. 7d is a schematic view showing a most stable conformation of an ester (13b).

(I) Preparation of Achiral Biaryl-Type Compounds

EXAMPLE 1

3-cyanocarbonyl-3'-methoxycarbonyl-2,2'-binaphthalene (1)

To a solution of 3-carboxy-3'-methoxycarbonyl-2,2'-binaphthalene (100 mg, 0.278 mmol) and thionyl chloride (SOCl$_2$) (24 μL, 0.334 mmol) in anhydrous benzene (6 mL) is added pyridine (10 μL, 0.124 mmol) with stirring, and the resulting suspension is further stirred at 50° C. for 1.5 hours.

As to 3-carboxy-3'-methoxycarbonyl-2,2'-binaphthalene, please see R. G. R. Bacon, R. Bankhead, J. Chem. Soc., 1963, pp. 839–845.

The resulting clear reaction solution is distilled off under a reduced pressure to obtain a crude acid chloride. Then, the crude acid chloride is dissolved in methylene dichloride (5 mL) and added with trimethylsilyl chloride (110 μL, 0.835 mmol) and a catalytic amount of zinc chloride, and thereafter the resulting mixed solution is stirred at 24° C. for 18.5 hours.

After the solvent is distilled off under a reduced pressure, the resulting crude product is purified through a recycle-type high-performance liquid chromatography (HPLC) (column: JAIGEL-H, CHCl$_3$) to obtain an acyl cyanide (1) (74 mg, 73%: in 2 steps 73%).

An outline of this synthesis reaction is shown by the following reaction formula:

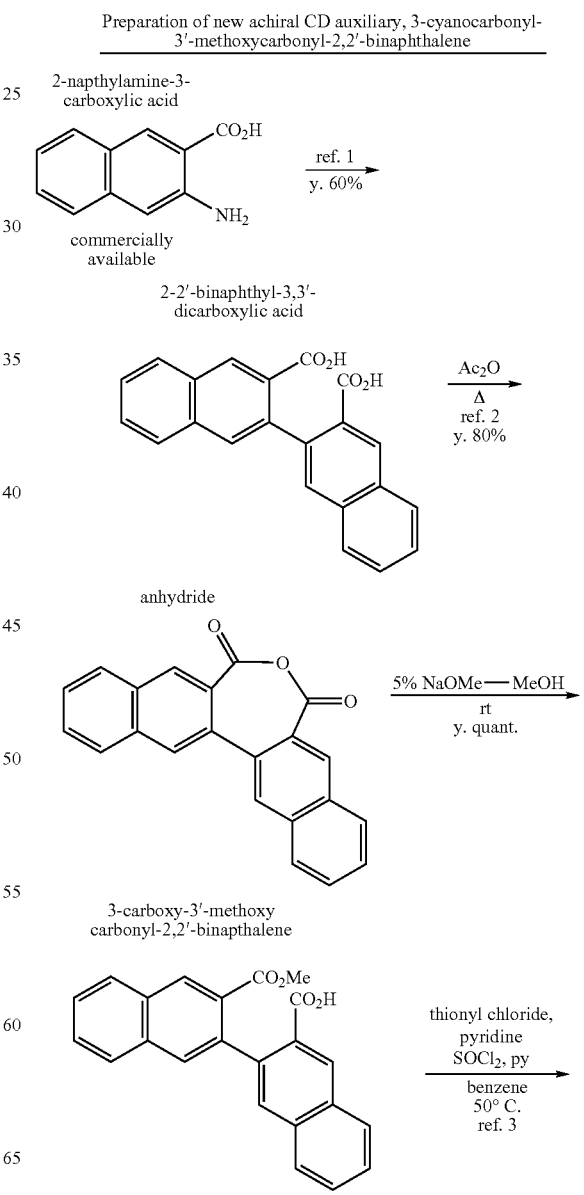

-continued

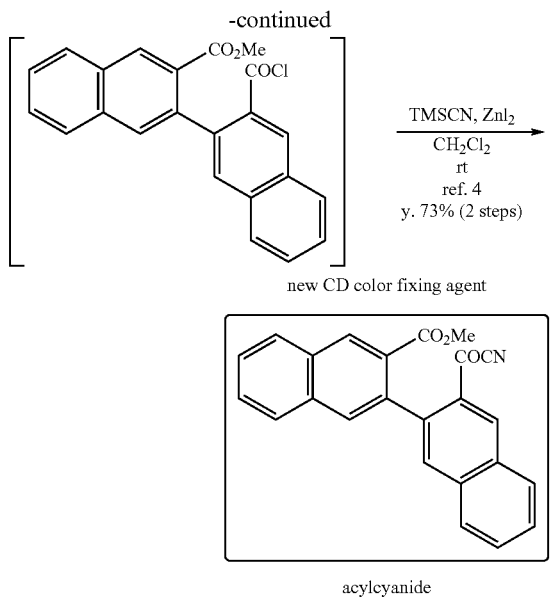

new CD color fixing agent

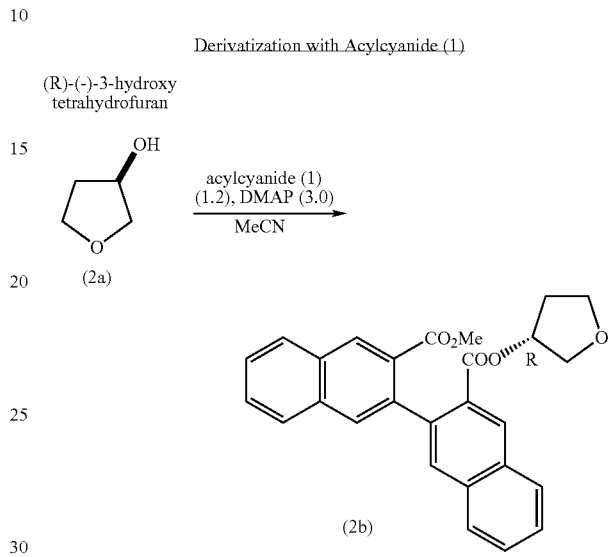

acylcyanide

References
1) E. J. Moriconi and L. Salce, J. Org. Chem. 32, 2829–2837(1967).
2) R. G. R. Bacon and R. Bankhead, J. Chem. Soc., 839–845(1963).
3) C. S. Marvel and L.A. Patterson, J. Am. Chem. Soc. 63, 2218–2220(1941).
4) J. Goto, N. Goto, F. Shamsa, M. Saito, S. Komatsu, K. Suzuki, T. Nambara, Anal. Chim. Acta, 147, 397–400(1983).

The acyl cyanide (1) is a yellow prism in nature and has the following physical properties.
(1) Molecular weight: 365 ($C_{24}H_{15}NO_3$)
(2) Melting point:.179–180.5° C.
(3) Rf value: 0.69 (hexane/ethyl acetate, 3/2 (v/v))
(4) Ultraviolet absorption spectrum (UV, $\lambda_{max}(\epsilon)$ nm, 1,4-dioxane): 371.5 (2500), 309.0 (13500), 262.5 (40900), 238.0 (66600)
(5) Infrared absorption spectrum (IR, $\nu_{max}$ cm$^{-1}$, chloroform): 3010 m, 2210 w, 1718 m, 1676 m, 1622 m, 1585 m, 1435 m, 1281 m, 1269 m, 1224 m, 1220 m, 1215 m, 1209 m, 1202 m, 1179 m, 1126 m, 1078 m, 988 m, 952 m, 929 m, 894 m, 783 m)
(6) Nuclear magnetic resonance spectrum ($^1$H-NMR, 500 MHz, δ, heavy chloroform): 8.86 (s, 1H), 8.68 (s, 1H), 8.13 (d, J=8.3 Hz, 1H), 8.02 (d, J=7.8 Hz, 1H), 7.89 (d, J=8.3 Hz, 1H), 7.85 (d, J=7.8 Hz, 1H), 7.75 (s, 1H), 7.74 (m, 1H), 7.72 (s, 1H), 7.70–7.58 (m, 3H), 3.72 (s, 3H)
(7) Nuclear magnetic resonance spectrum ($^{13}$C-NMR, 125 MHz, δ, heavy chloroform): 167.6, 166.9, 138.5, 137.6, 137.1, 136.0, 134.8, 132.0, 131.9, 131.4, 131.1, 130.9, 130.6, 129.9, 129.7, 129.1, 128.8, 127.9, 127.7, 127.6, 127.0, 113.3, 52.0
(8) Mass spectrum (MS, m/z (relative intensity, %)): 365 (M$^+$, 85), 312 (23), 311 (100), 307 (20), 306 (76), 296 (12), 281 (12), 280 (49), 278 (11), 277 (30), 252 (17), 250 (17), 126 (12)
(9) Elementary analysis: calculated value (C: 78.89, H: 4.14, N: 3.83), found value (C: 78.80, H: 4.14, N: 3.81).

(II) Derivative Formation of Chiral Compound

EXAMPLE 2

To a solution of (R)-(−)-3-hydroxytetrahydrofuran (2a) (1.8 μL, 0.0228 mmol) and acyl cyanide (1) prepared in Example 1 (10 mg, 0.0274 mmol) in acetonitrile (0.5 mL) is added 4-dimethylaminopyridine (DMAP) (8.4 mg, 0.0687 mmol) and the resulting mixed solution is stirred at room temperature under an argon atmosphere for 5 hours.

After the solvent is distilled off under a reduced pressure, the resulting crude product is purified through a silica gel chromatography (eluent: chloroform) to obtain binaphthyl ester (2b) (9.6 mg, 100%).

An outline of this synthesis reaction is shown by the following reaction formula:

Derivatization with Acylcyanide (1)

The binaphthyl ester (2b) is a colorless prism (from ethyl acetate) in nature and has the following physical properties.
(1) Molecular weight: 426 ($C_{27}H_{22}NO_5$)
(2) Melting point: 147.5–149.5° C.
(3) Rf value: 0.51 (hexane/ethyl acetate, 1/1 (v/v))
(4) Ultraviolet absorption spectrum (UV, $\lambda_{max}(\epsilon)$ nm, cyclohexane): 244.0 (81900), 340.0 (2300)
(5) Circular dichroism spectrum (CD) ($\lambda_{ext}(\Delta\epsilon)$ nm, cyclohexane): 228.8 (−6.1), 236.9 (0), 245.0 (+6.6)
(6) Infrared absorption spectrum (IR, $\nu_{max}$ cm$^{-1}$, chloroform): 3005 w, 2940 m, 1721 s, 1621 w, 1583 m, 1486 w, 1433 m, 1343 w, 1319 w, 1279 s, 1220 m, 1218 m, 1201 m, 1132 m, 1097 m, 1057 m, 1008 m, 977 w, 951 w, 907 m, 891 m, 782, w
(7) Nuclear magnetic resonance spectrum ($^1$H-NMR, 500 MHz, δ, heavy chloroform): 8.62 (s, 1.5 H), 8.61 (s, 0.5 H), 8.00 (brd, J=7.8 Hz, 1 H), 7.99 (brd, J=7.8 Hz, 1 H), 7.86 (brs, 1 H), 7.85 (brs, 1 H), 7.77 (s, 0.5 H), 7.76 (s, 0.5 H), 7.75 (s, 0.5 H), 7.74 (s, 0.5 H), 7.59 (m, 4 H), 5.26 (m, 1 H), 3.80 (quint, J=5.4 Hz, 1 H), 3.68–3.44 (m, 3 H), 3.66 (s, 3 H), 1.97 (m, 1 H), 1.65 (m, 1 H)
(8) Mass spectrum (MS, m/z (relative intensity, %)): 426 (M$^+$, 91), 357 (25), 356 (100), 339 (24), 312 (23), 311 (32), 297 (23), 296 (25), 295 (43), 282 (19), 281 (72), 280 (78), 268 (15), 253 (16), 252 (49), 250 (20), 239 (30)
(9) High resolution mass spectrum: calculated value (426.1467), found value (426.1472),
(10) Specific rotation: $[\alpha]^{24}_D$+12.4° (c 0.043, chloroform).

EXAMPLE 3

A binaphthyl ester (2b) is prepared by changing the acyl cyanide (1) (1.2 mol equivalent) in Example 2 with acyl cyanide (1) (1.1 mol equivalent). The yield is 96%.

EXAMPLES 4–8

An influence of a base upon a yield of a derivative is investigated.

The same procedure as in Example 3 is repeated except that DMAP (3 mol equivalent) in Example 3 is changed to Example 4: pyridine (3 mol equivalent), Example 5: DBU (1,8-diazabicyclo[5.4.0]undeca-7-ene, 3 mol equivalent), Example 6: Et$_3$N (3 mol equivalent), Example 7: 50% Et$_3$N/MeCN, and Example 8: 5% Et$_3$N /MeCN, respectively, and the reaction temperature and reaction time are changed as shown in Table 3.

TABLE 3

| Example | Base (mol equiv.) | Temperature | Time(hr) | Yield(%) |
|---|---|---|---|---|
| 2 | DMAP(3.0)*[1] | Room temp.(25° C.) | 5 | 100 |
| 3 | DMAP(3.0) | Room temp.(25° C.) | 5 | 96 |
| 4 | Pyridine(3.0) | Room temp.(25° C.) | 72 | 27 |
| 5 | DBU(3.0) | Room temp.(25° C.) | 5 | 92 |
| 6 | Et$_3$N(3.0) | Room temp.(25° C.) | 5 | 71 |
| 7 | 50% Et$_3$N/MeCN | 60° C. | 2 | 65 |
| 8 | 5% Et$_3$N/MeCN | 60° C. | 2 | 67 |

*[1] acylcyanide (1) (1.2 mol equiv.) was used.

As shown in Table 3, a best yield is obtained in a combination of acyl cyanide (1) (1.2 mol equivalent) and base, DMAP (3.0 mol equivalent) of Example 2.

(III) Derivatives of Saturated Alcohol (Group A)

EXAMPLES 9 AND 10

A saturated chiral secondary alcohol (Example 9: l-menthol (3a) and Example 10: d-menthol (4a)) is reacted with acyl cyanide (1) prepared in Example 1 under the presence of DMAP in MeCN instead of (R)-(−)-3-hydroxy tetrahydrofuran (2a) of Example 2 in the same manner as in Example 2.

Each of the reactions is shown by the following reaction formulae:

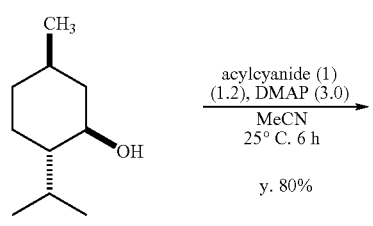

l-Menthol
(3a)

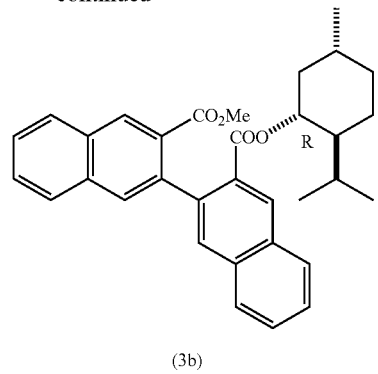

d-Menthol
(4a)

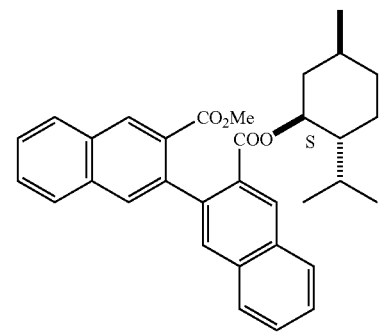

According to each of the reactions, corresponding esters (3b) and (4b) are obtained with good yields of 80% and 84%, respectively. A $^1$H-NMR (CDCl$_3$) and a CD spectrum (in cyclohexane) of each ester are measured to obtain results as shown in FIGS. 3–5.

As shown in FIGS. 3 and 4, the esters (3b) and (4b) show the same $^1$H-NMR spectrum in CDCl$_3$. As shown in FIG. 5, the esters (3b) and (4b) are symmetric in the CD spectrum. As seen from these results, the esters (3b) and (4b) have an enantiomeric relation mutually in the solution.

The CD spectra of the thus obtained esters show a split-type cotton effect as is expected, and give a relatively large amplitude.

With respect to these esters, the ultraviolet absorption spectra (UV, $\lambda_{max}(\epsilon)$ nm, cyclohexane) and the circular dichroism spectrum (CD) ($\lambda_{ext}(\Delta\epsilon)$ nm, cyclohexane) are measured in the same manner as in Example 2. And also, a relation between a sign of exciton chirality and an absolute configuration with respect to each ester is examined. The results are shown in Table 4.

EXAMPLES 11–16

The following chiral alcohols (5a)–(10a) are esterified in the same manner as in Example 9.

Example 11: (S)-2-octanol (5a), Example 12: (R)-2-octanol (6a), Example 13: (1S, 2S, 3S, 5R)-(−)-isopinocampheol (7a), Example 14: (1R, 2R, 3R, 5S)-(−)-isopiriocampheol (8a), Example 15: β-cholestanol (9a) and Example 16: α-cholestanol (10a).

The following formulae show esters (5b)–(10b) corresponding to the chiral alcohols (5a)–(10a).

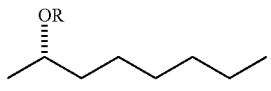
(5b)

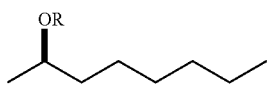
(6b)

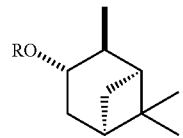
(7b)

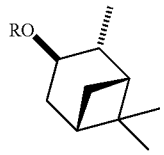
(8b)

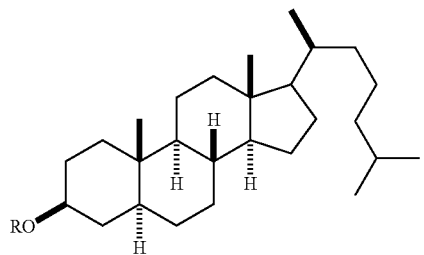
(9b)

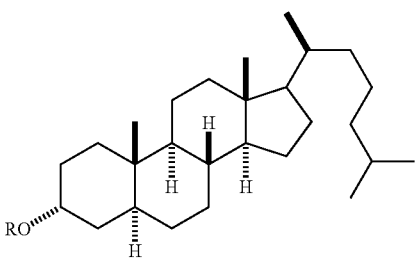
(10b)

Moreover, R in the above formulae is a group represented by the following formula (XIII).

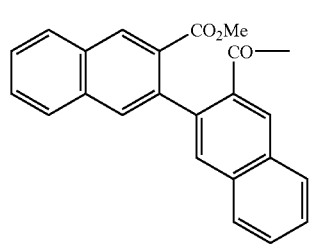
(XIII)

The yield, ultraviolet absorption spectrum (UV, $\lambda_{max}(\epsilon)$ nm, cyclohexane), circular dichroism spectrum (CD) ($\lambda_{ext}$ ($\Delta\epsilon$) nm, cyclohexane) and relation between sign of exciton chirality and absolute configuration with respect to each of the esters (5b)–(10b) are shown in Table 4.

TABLE 4

| Example | Ester[*a] | Yield (%)[*b] | UV $\lambda_{max}$(nm)($\epsilon$)[*c] | CD $\lambda_{ext}$(nm)($\Delta\epsilon$)[*c] | Exciton chirality | Absolute config. |
|---|---|---|---|---|---|---|
| 9 | 3b | 80 | 243.5 (69700) 339.5 (4500) | 227.1 (+22.4) 235.9 (0) 248.1 (−17.2) | − | R |
| 10 | 4b | 84 | 243.5 (75600) 339.5 (4800) | 226.5 (−23.7) 236.0 (0) 247.4 (+19.1) | + | S |
| 11 | 5b | 70 | 243.0 (91200) 338.5 (2700) | 228.0 (−23.0) 235.7 (0) 244.8 (+21.7) | + | S |
| 12 | 6b | 82 | 243.0 (97200) 339.0 (3000) | 228.2 (+25.1) 235.6 (0) 243.8 (−23.1) | − | R |
| 13 | 7b | 84 | 243.5 (86300) 339.5 (2100) | 220.5 (−2.5) 241.8 (0) 245.5 (+1.9) | + | S |
| 14 | 8b | 100 | 243.5 (81400) 339.5 (2000) | 221.1 (+2.0) 240.6 (0) 245.4 (−1.7) | − | R |
| 15 | 9b | 54 | 243.0 (81600) 339.0 (2400) | 233.3 (−6.1) 238.2 (0) 247.0 (+9.3) | + | S |

TABLE 4-continued

| Example | Ester*a | Yield (%)*b | UV $\lambda_{max}$(nm)($\epsilon$)*c | CD $\lambda_{ext}$(nm)($\Delta\epsilon$)*c | Exciton chirality | Absolute config. |
|---|---|---|---|---|---|---|
| 16 | 10b | 43 | 244.5 (69900) 339.0 (3800) | 232.9 (+8.3) 242.2 (0) 247.6 (−2.8) | − | R |

*a 3.0 equiv. of base was added to a solution of alcohol and 1.2 equiv. of acylcyanide (1) in CH$_3$CN and the reaction was carried out at room temperature.
*b Isolated yield.
*c Measured in cyclohexane.

As shown in Table 4, the signs of exciton chirality of the thus obtained esters are observed to have a good interrelation to the absolute configurations of the various chiral secondary alcohols. That is, R body shows minus, and S body shows plus.

(IV) Derivatives of Unsaturated Alcohols (Group B)

EXAMPLES 17–20

Instead of (R)-(−)-3-hydroxy tetrahydrofuran (2a) of Example 2, unsaturated chiral secondary alcohols (11a)–(14a) are esterified as follows.

Each of Example 17: (S)-(+)-3-hydroxy tetrahydrofuran (11a), Example 18: (R)-(+)-4-chloro-3-hydroxy butyronitrile (12a), Example 19: (S)-(−)-4-chloro-3-hydroxy butyronitrile (13a) and Example 20: 17,18-dihydroxy bergamottin (14a) is reacted with acyl cyanide (1) prepared in Example 1 under the presence of DMAP in MeCN in the same manner as in Example 2.

Moreover, 17,18-dihydroxy bergamottin isolated from grapefruit juice is used. This compound has a CYP3A4 inhibiting activity.

The following formulae show esters (11b)–(14b) corresponding to the chiral alcohols (11a)–(14a).

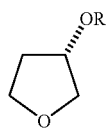
(11b)

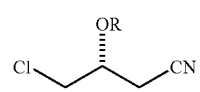
(12b)

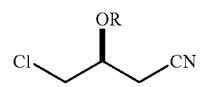
(13b)

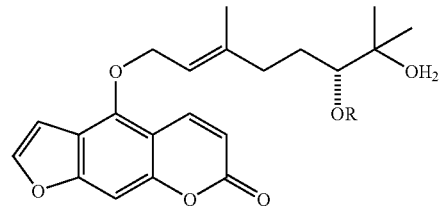
(14b)

Moreover, R in the above formulae is the same as the formula (XIII).

With respect to the esters (2b) and (11b)–(14b), the yield, ultraviolet absorption spectrum (UV, $\lambda_{max}$($\epsilon$) nm, cyclohexane), circular dichroism spectrum (CD) ($\lambda_{ext}$($\Delta\epsilon$) nm, cyclohexane) and relation between sign of exciton chirality and absolute configuration of the each of esters (2b) and (11b)–(14b) are shown in Table 5.

TABLE 5

| Example | Ester*a | Yield (%)*b | UV $\lambda_{max}$(nm)($\epsilon$)*d | CD $\lambda_{ext}$(nm)($\Delta\epsilon$)*d | Exciton chirality | Absolute config. |
|---|---|---|---|---|---|---|
| 2 | 2b | 100 | 244.0 (81900) 340.0 (2300) | 228.8 (−6.1) 236.9 (0) 245.0 (+6.6) | + | R |
| 17 | 11b | 100 | 244.0 (84700) 339.0 (3800) | 229.1 (+7.0) 236.9 (0) 245.4 (−8.1) | − | S |
| 18 | 12b | 100 | 245.0 (81200) 339.0 (2900) | 231.3 (−8.1) 237.2 (0) 243.0 (+8.4) | + | R |
| 19 | 13b | 100 | 245.0 (77800) 338.5 (2800) | 229.6 (+8.0) 237.4 (0) 242.7 (−8.0) | − | S |
| 20 | 14b | 45*c | 245.0 (60500) 285.0 (13000) | 235.4 (−5.6) 241.8 (0) 246.7 (+2.8) 256.6 (0) | + | R |

*a 3.0 equiv. of base was added to a solution of alcohol and 1.2 equiv. of acylcyanide (1) in CH$_3$CN and the reaction was carried out at room temperature.
*b Isolated yield.
*c The recovery rate of starting material was 43%.
*d Measured in cyclohexane.

As shown in Table 5, the exciton chiralities of the thus obtained esters are recognized to have a good interrelation to the absolute configurations of the various unsaturated chiral secondary alcohols in opposition to the cases of the saturated alcohols. That is, R body shows plus, and S body shows minus. According to this relation, the absolute configuration of 17,18-dihydroxy bergamottin is determined to be R configuration.

(V) Most Stable Conformation Found by Molecular Force-Field Calculation

The most stable conformations of the esters (3b), (4b), (5b) and (6b) in the saturated alcohols (group A) and the most stable conformations of the esters (2b), (11b), (12b) and (13b) in the unsaturated alcohols (group B) are measured according to a molecular filed-force calculation (CONFLEX).

The results are shown in FIGS. 6a–d and FIGS. 7a–d, respectively. In FIGS. 6 and 7, R group is the same as the group of formula (XIII).

As shown in FIGS. 6 and 7, the results indicated in Tables 4 and 5 are supported by torsional directions of two naphthalene rings in the most stable conformation.

The above results show that an asymmetry of carbinol carbon is recognized and a chirality inherent to alcohol is effectively propagated to a binaphthyl part as a chromophore.

(VI) Derivative Formation of Chiral Compound with Binaphthyl Carboxylic Anhydride

EXAMPLES 21–24

Various chiral secondary alcohols as mentioned later are reacted with 2,2'-binaphthyl-3,3'-dicarboxylic anhydride under the presence of DMAP in THF and methylated with $CH_2N_2/Et_2O$-MeOH.

Example 21: l-menthol, Example 22: d-menthol, Example 23: (R)-2-octanol, Example 24: (S)-2-octanol.

Each of the reactions is shown by the following reaction formulae:

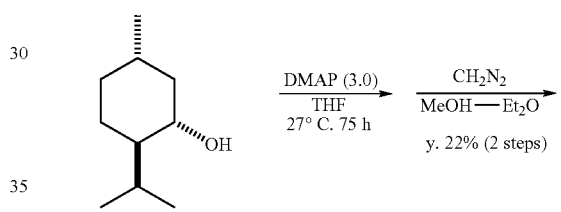

-continued

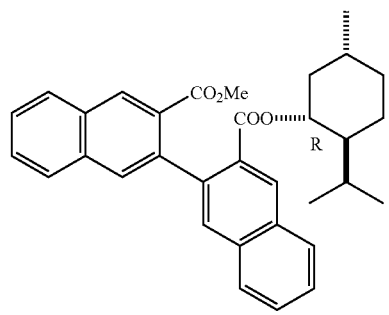

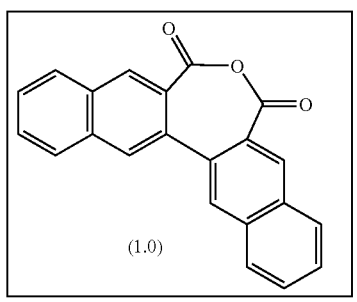

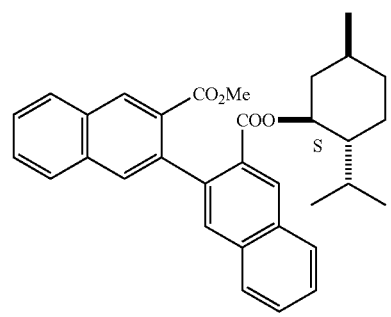

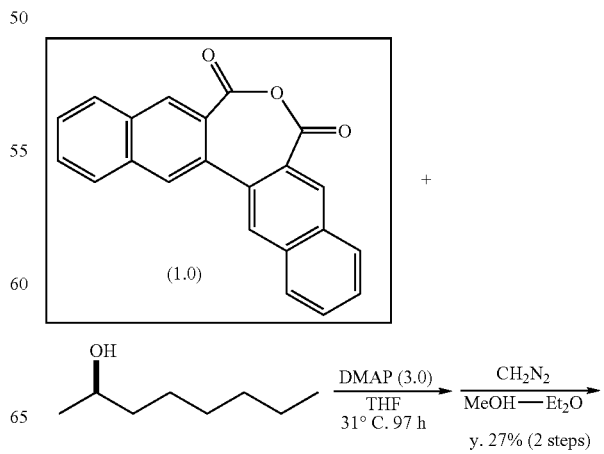

-continued

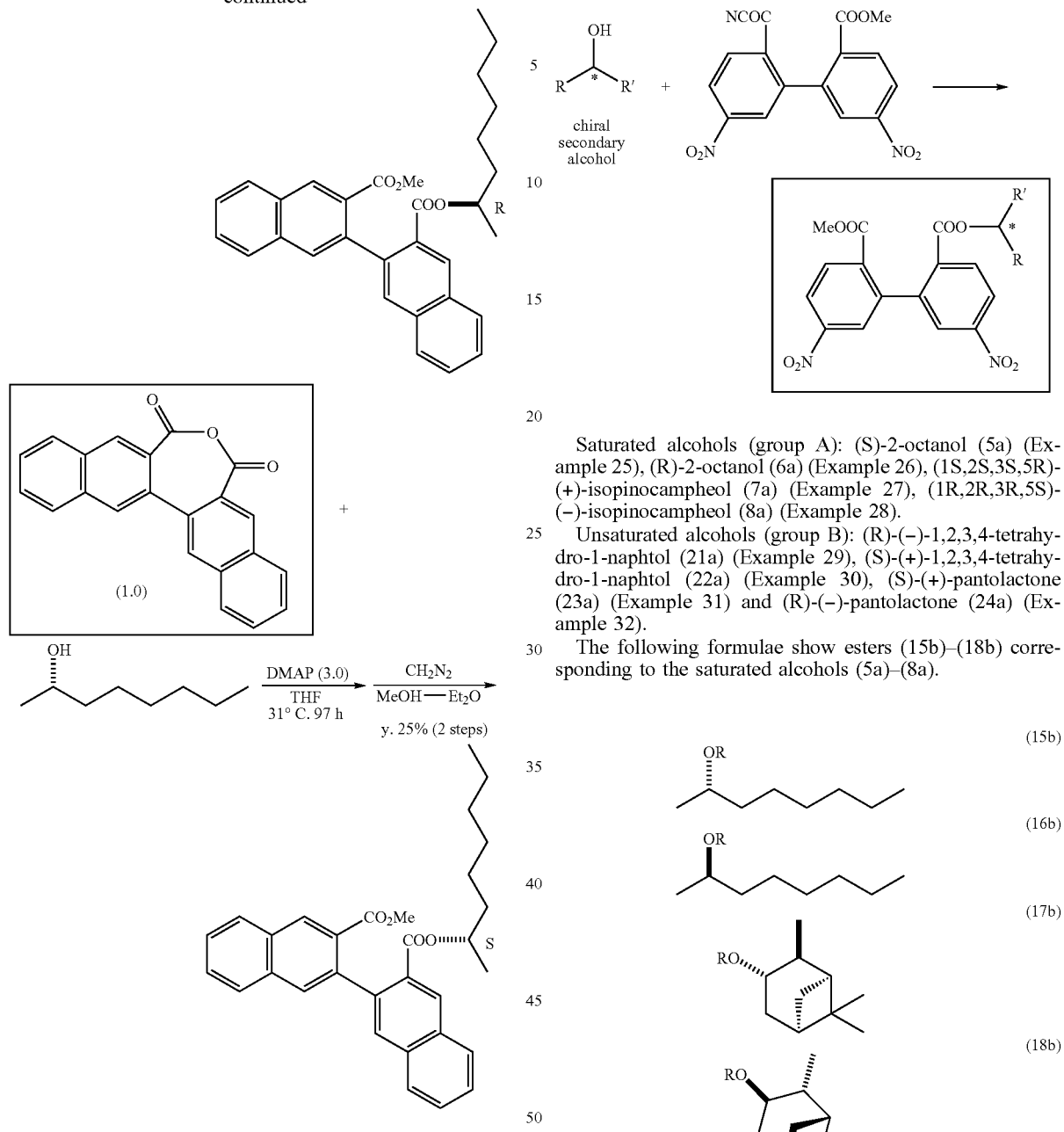

The formation of derivatives of chiral compound may be carried out even by two-stage reaction using a binaphthyl carboxylic anhydride.

The corresponding esters are obtained in yields of 18, 22, 27 and 25%, respectively, though these yields are lower than that of the reaction with acyl cyanide (1).

(VII) Derivative Formation of Chiral Compound with a Biphenyl Dicarboxylic Acid Derivative

EXAMPLES 25–32

Derivatives of the following saturated alcohols (group A) and unsaturated alcohols (group B) are formed by using 2-cyanocarbonyl-2'-methoxycarbonyl-5,5'-dinitro-1,1'-biphenyl.

An outline of the reaction is shown by the following reaction formula:

Saturated alcohols (group A): (S)-2-octanol (5a) (Example 25), (R)-2-octanol (6a) (Example 26), (1S,2S,3S,5R)-(+)-isopinocampheol (7a) (Example 27), (1R,2R,3R,5S)-(−)-isopinocampheol (8a) (Example 28).

Unsaturated alcohols (group B): (R)-(−)-1,2,3,4-tetrahydro-1-naphtol (21a) (Example 29), (S)-(+)-1,2,3,4-tetrahydro-1-naphtol (22a) (Example 30), (S)-(+)-pantolactone (23a) (Example 31) and (R)-(−)-pantolactone (24a) (Example 32).

The following formulae show esters (15b)–(18b) corresponding to the saturated alcohols (5a)–(8a).

Moreover, R in the above formulae is a group represented by the following formula (XIV):

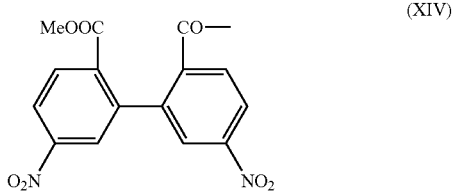

The following formulae show esters (21b)–(24b) corresponding to the unsaturated alcohols (21a)–(24a).

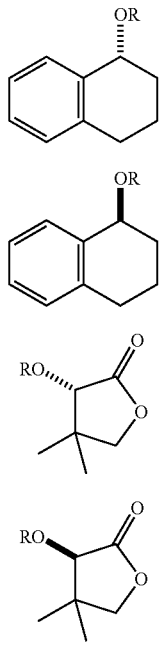

Moreover, R in the above formulae is the same group as the formula (XIV).

The thus obtained esters are recognized to have a good interrelation between the cotton effect and the absolute configuration of each of the various saturated and unsaturated chiral secondary alcohols. That is, the sign of the cotton effect at about 270 nm with respect to the esters (15b)–(18b) corresponding to the saturated alcohols is minus in R body and plus in S body, and the sign of the cotton effect at about 270 nm with respect to the esters (21b)–(24b) corresponding to the unsaturated alcohols is plus in R body and minus in S body.

The achiral biaryl-type compound, especially CD color fixing agent according to the invention simply forms a derivative of a chiral compound as a substrate in a high yield, and is possible to very efficiently determine an absolute configuration.

And also, the method for the determination of absolute configuration according to the invention does not require the molecular force-field calculation as in the conventional method and can determine an absolute configuration of a chiral compound directly from a correlation among relative bulkiness of a substituent on α-carbon, preferential order in a sequence rule and sign of exciton chirality.

What is claimed is:

1. An achiral biaryl-type compound in which the biaryl-type compound is at least one compound selected from 2, 2'-binaphthyl dicarboxylic acid derivative represented by the following general formula (II):

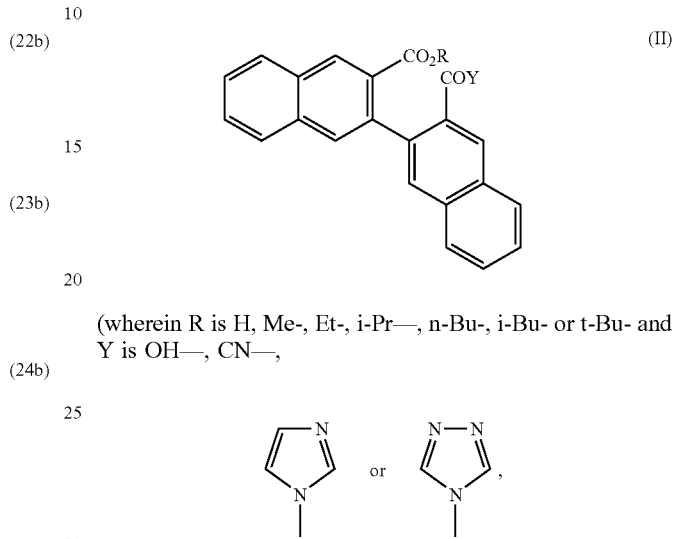

(wherein R is H, Me-, Et-, i-Pr—, n-Bu-, i-Bu- or t-Bu- and Y is OH—, CN—, provided that R is i-Pr—, n-Bu-, i-Bu- or t-Bu- when Y=OH).

2. A circular dichroism,(CD) color fixing agent for introducing an achiral CD chromophore into a chiral compound, in which the chiral compound is selected from the group consisting of alcohols, thiols and amines, and the CD color fixing agent comprises at least one achiral biaryl-type compound selected from the group consisting of 2,2'-binaphthyl dicarboxylic acid, of formula (II) according to claim 1.

3. A method for determining an absolute configuration of a chiral compound, which comprises steps of:
   (a) selecting a chiral compound from the group consisting of alcohols, thiols and amines;
   (b) introducing an achiral CD chromophore into the chiral compound of formula (II) according to claim 1; and
   (c) determining an absolute configuration of the chiral compound from relative bulkiness of a substituent on α-carbon, preferential order in a sequence rule (CIP method) and sign of exciton chirality.

* * * * *